(12) United States Patent
Monnier et al.

(10) Patent No.: US 11,630,230 B2
(45) Date of Patent: Apr. 18, 2023

(54) SYSTEM AND METHOD FOR SCANNING A PERSON BEFORE ENTRY TO A RESTRICTED ACCESS AREA

(71) Applicant: SEDECT SA, Gland (CH)

(72) Inventors: Frédéric Monnier, Cortaillod (CH); Marc Lany, Rolle (CH); Luis Filipe Soldado Granadeiro Rosado, Gland (CH); Gilles Santi, Lausanne (CH); Bernard Revaz, Genèva (CH); Alain Berthoud, Châtelaine (CH)

(73) Assignee: Sedect SA, Gland (CH)

( * ) Notice: Subject to any disclaimer, the term of this patent is extended or adjusted under 35 U.S.C. 154(b) by 312 days.

(21) Appl. No.: 16/461,673

(22) PCT Filed: Nov. 22, 2017

(86) PCT No.: PCT/IB2017/057341
§ 371 (c)(1),
(2) Date: May 16, 2019

(87) PCT Pub. No.: WO2018/096473
PCT Pub. Date: May 31, 2018

(65) Prior Publication Data
US 2019/0353817 A1    Nov. 21, 2019

(30) Foreign Application Priority Data
Nov. 24, 2016  (CH) ........................................ 1554/16

(51) Int. Cl.
*G01V 3/12*    (2006.01)
*G01N 33/00*   (2006.01)
(Continued)

(52) U.S. Cl.
CPC ........... *G01V 3/12* (2013.01); *G01N 33/0057* (2013.01); *G01V 3/105* (2013.01); *G01V 3/15* (2013.01); *G07C 9/37* (2020.01)

(58) Field of Classification Search
None
See application file for complete search history.

(56) References Cited

U.S. PATENT DOCUMENTS 5,680,103 A * 10/1997 Turner .................. G01V 3/105
                                                    324/243
6,057,761 A *  5/2000 Yukl ..................... A61B 5/0507
                                                    250/358.1
(Continued)

FOREIGN PATENT DOCUMENTS

DE     29813997 U1    10/1998
EP      0978734 A2     2/2000
(Continued)

OTHER PUBLICATIONS

Translation of DE 29813997 (Year: 1998).*
International Search Report & Written Opinion for PCT/IB2017/057341; dated Feb. 22, 2018, 10 pages.

*Primary Examiner* — Christopher P McAndrew
*Assistant Examiner* — Mustafizur Rahman
(74) *Attorney, Agent, or Firm* — Blank Rome LLP

(57) ABSTRACT

The invention concerns a system (1) and a method for scanning a person (2) before access to a restricted access area (3), comprising a processing unit (14) and a metal detector (10, 70) for detecting metal in the shoes (20) or in a waist portion of the person walking on a surface (15). The processing unit controls an indication unit (12, 13) for: letting the person walk towards the restricted area if a first scan indicates the probability of the presence of metal lower than a first threshold; in case of a probability higher than the first threshold, prompting the person to carry out a second (Continued)

scan close to a mark (11) on the carpet; and prompting the user to remove his shoes or object if the first scan indicates a probability higher than a second threshold, or if the second scan indicates a probability higher than a third threshold.

15 Claims, 5 Drawing Sheets

(51) Int. Cl.
  *G01V 3/10* (2006.01)
  *G01V 3/15* (2006.01)
  *G07C 9/37* (2020.01)

(56) References Cited

U.S. PATENT DOCUMENTS

| | | | |
|---|---|---|---|
| 6,094,472 A * | 7/2000 | Smith | G01N 23/203 378/86 |
| 6,970,087 B2 | 11/2005 | Stis | |
| 7,053,785 B2 | 5/2006 | Akins | |
| 7,327,137 B1 * | 2/2008 | Crowley | G01R 33/441 324/300 |
| 7,352,180 B2 | 4/2008 | Manneschi | |
| 9,277,897 B1 * | 3/2016 | Linev | A61B 6/4078 |
| 2004/0222790 A1 * | 11/2004 | Karmi | G01R 33/441 324/309 |
| 2005/0146441 A1 * | 7/2005 | Akins | G01V 3/08 340/693.5 |
| 2008/0111545 A1 * | 5/2008 | Crowley | G01V 3/101 324/234 |
| 2010/0141502 A1 * | 6/2010 | Cardiasmenos | G01N 21/3581 342/22 |
| 2010/0213365 A1 * | 8/2010 | Crowley | G01N 24/084 250/282 |
| 2011/0026674 A1 * | 2/2011 | Rothschild | G01V 5/0016 378/57 |
| 2011/0129063 A1 | 6/2011 | Bendahan | |
| 2012/0307968 A1 * | 12/2012 | Smith | G01V 5/0016 378/57 |
| 2014/0063239 A1 * | 3/2014 | Furness, III | G01N 21/31 348/143 |
| 2014/0070946 A1 * | 3/2014 | Ambrefe, Jr. | H04W 4/029 340/541 |
| 2014/0185755 A1 * | 7/2014 | Bendahan | G01V 5/0025 378/57 |
| 2015/0253422 A1 * | 9/2015 | Morton | G01S 13/887 324/642 |

FOREIGN PATENT DOCUMENTS

| | | |
|---|---|---|
| EP | 1411373 A2 | 4/2004 |
| EP | 2224268 A2 | 9/2010 |

* cited by examiner

SYSTEM AND METHOD FOR SCANNING A PERSON BEFORE ENTRY TO A RESTRICTED ACCESS AREA

RELATED APPLICATIONS

This application is a national phase of PCT/IB2017/057341, filed on Nov. 22, 2017, which claims priority to Swiss Application No. CH01554/16, filed on Nov. 24, 2016. The entire contents of these applications are hereby incorporated by reference.

FIELD OF THE INVENTION

The present invention concerns a system and a method for scanning a person before entry to a restricted access area, notably a passenger before entering a restricted area of an airport, bus station, train station, building, etc.

DESCRIPTION OF RELATED ART

The prevention of accidental and malicious harm and the repression of illegal and criminal acts often imply the creation of restricted access areas in sensitive facilities and buildings. Such restricted access areas are provided at their entry points with security scanning systems for detecting dangerous and illegal objects worn or carried by persons wanting to access the restricted area.

Transportation for example, airports are provided with security systems for protecting passengers, staff and vehicles from accidental and malicious harm (e.g. airport security).

In order to scan all the persons entering such a restricted area, it is common to provide an access path that forces all persons to go through a security portal with a metal detector. If metal is detected, a further body scan is performed manually or with a body scanner.

In the domain of the security, it is known that shoes and footwear can provide hiding places for carrying dangerous and illegal objects. Shoes also frequently incorporate metal parts, such as reinforcements, and create a lot of false positive results. When metal is detected, the person is often required to remove his shoes, put them in a tray on a conveyor, and go through the portal a second time without his shoes. This move back to the conveyor creates a non-laminar flow of persons in the queue and dramatically increases the waiting time for the next persons.

In order to avoid this need for double scanning of some passengers, some airports require all passengers to remove their shoes and put them in a tray in advance. However, the shoe removal process causes great inconvenience and further delays in the queue.

Devices for scanning shoes separately are also known in the prior art. As an example, U.S. Pat. No. 7,352,180 discloses a device for detecting non-authorized material in shoes, the detection being based on Nuclear Magnetic Resonance. This device is expensive and requires an accurate positioning of the shoe of the individual relative to the detector.

US2011/0129063 discloses an X-ray inspection system for shoes. This system eliminates the need for the persons to remove their shoes. However, this system requires an operator to analyze the images of the shoes. Moreover, X-Ray scanning all passengers exposes them to ionizing radiation which is undesirable for health reasons.

U.S. Pat. No. 6,970,087 and EP1411373 disclose devices having recesses for receiving both feet of the user so as to simultaneously scan both his shoes for metal objects. Requesting all persons to precisely position both shoes onto a detector is not user-friendly and creates an additional delay in the queue and an operator to instruct the users.

US2004/0222790 discloses a detector of threat material in shoes. A screening process is activated manually or automatically when the device senses the presence of a measurable object. In one embodiment, the device comprises an antenna coil under or in the top of the detection device onto which the person has to step for accessing the restricted area. The device performs its measurements and provides one or more indications on an output device. For example, such an indication may be visual in the form of a light: green for no threat, red upon threat detection and yellow when results are inconclusive and the measurement must be repeated.

EP0978734 describes a metal detector for detecting metal objects in shoes. The detector is hidden in a carpet and not seen by the users. An acoustic or optical signal is emitted when a metallic object is detected.

Those prior-art detecting devices and methods are configured to detect metal parts or other threats in the most reliable way, since the safety of the restricted area depends on an unfailing detection. Therefore, those devices are expensive, and subject to rapid obsolescence due to the constant apparition of new dangerous and illegal objects. They often create a lot of false positive results, i.e., often output a detection signal even in the absence of any threat. Treating these false positives requires a manual inspection which creates unwanted delays for the next persons in the queue. Moreover, those devices need to be approved and periodically inspected to make sure that they are operating correctly. As a consequence, their deployment is slow.

In many situations, the reliable detection of metal parts on the persons is already made by a security portal and those additional detectors for shoes are redundant, creating additional costs, without increasing security. Therefore, most airports do not use additional devices for the detection of threats in shoes.

Nevertheless, it would be desirable to detect before the security portal at the entrance to a restricted area those persons who have metal parts in their shoes, and who need to remove their shoes. This would avoid the need for other persons to remove their shoes, and reduce the delays created by a person who needs to go back, remove the shoes, and pass through the security portal a second time after a metal detection.

In order to address the problem, U.S. Pat. No. 7,053,785 discloses a pre-screening device which may alert persons subjected to a screening process that their shoes may contain enough material to set off the alarm of a metal detector. In this way, the individual may take the proper steps to avoid an alarm caused by their shoes. Similarly, individuals without sufficient material present in their shoes to set off an alarm may proceed through the screening process without delay. This device requires the user to place his shoe in a compartment of the metal detector. Precisely positioning one shoe in this compartment creates an additional delay for all persons in the queue.

BRIEF SUMMARY OF THE INVENTION

The aim of the invention is to provide a system and a method avoiding, or at least reducing some of, those problems of the prior art.

In particular, an aim is to provide a system and a method for detecting the persons in a queue who need to remove their shoes and for allowing the others to move on directly to a security portal.

An aim is to provide a system and a method for detecting metal in shoes worn by persons in a queue in a non-obstructive way, and with minimal or no delay.

Another aim is to provide a solution not subject to rapid technical obsolescence.

According to the invention, these aims are achieved by means of the system of claim 1 and the method of claim 10.

This method and system permit a more rapid flow of people at, and trough, a security portal of a restricted access area.

Since the reliability of the detection is ensured by the security portal which is used in any case, the device could be relatively simple and does not require the precise positioning of the user's feet with respect to the detection means. Moreover, the device does not need to be approved or inspected, since the security of the restricted area does not depend on it.

The proposed solution provides early assessment of the potential presence of metallic objects within the shoes worn by persons so as to prompt the person to remove his shoes before going through the security portal for the first time. The removal of potential problematic shoes facilitates the flow of the users through the security portal because an earlier removal of critical shoes reduces the number of persons who stop the flow of persons due to having to come back through the security portal. It is to notice that quite a lot of persons are wearing shoes with inoffensive metallic components or garnishes that would trigger an alarm when passing through the security portal.

The two-stage scanning of the shoes worn by the person, i.e. a first (or pre-scanning) of the shoes worn by the user walking on a path to the security portal followed, in case of inconclusive results, by a second scan (or rescanning) of the shoes at a predefined position, contributes to a rapid and comfortable passage of the flow of persons through the security portal. In fact, only the persons wearing shoes considered problematic are affected by the second scan that requires a predefined positioning of the worn shoes with respect to the detector.

The two-stage scanning of the shoes worn by the person, i.e. the first (or pre-scanning) and the second scan (or rescanning) of the shoes located at a predefined position by means of the same metal detector, contributes to provide a compact and cost-effective solution, while facilitating the installation and the cooperation of the system with existing access paths and security portals.

The solution further provides a reliable security scan of persons while not being subject to technical obsolescence. In fact, the solution provides the suspicion of the problematic presence of a metal object while the detection of dangerous and illegal objects worn or carried by the user relies on the security portal scanning. Advantageously, the scan of the shoes relies on dedicated, invasive and/or potentially harmful detection systems that could provide more accurate detection of illegal and dangerous objects and substances (e.g. X-ray based systems).

The solution is further compatible with existing access paths and security portals of facilities and buildings, without requiring complex and bulky installations.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
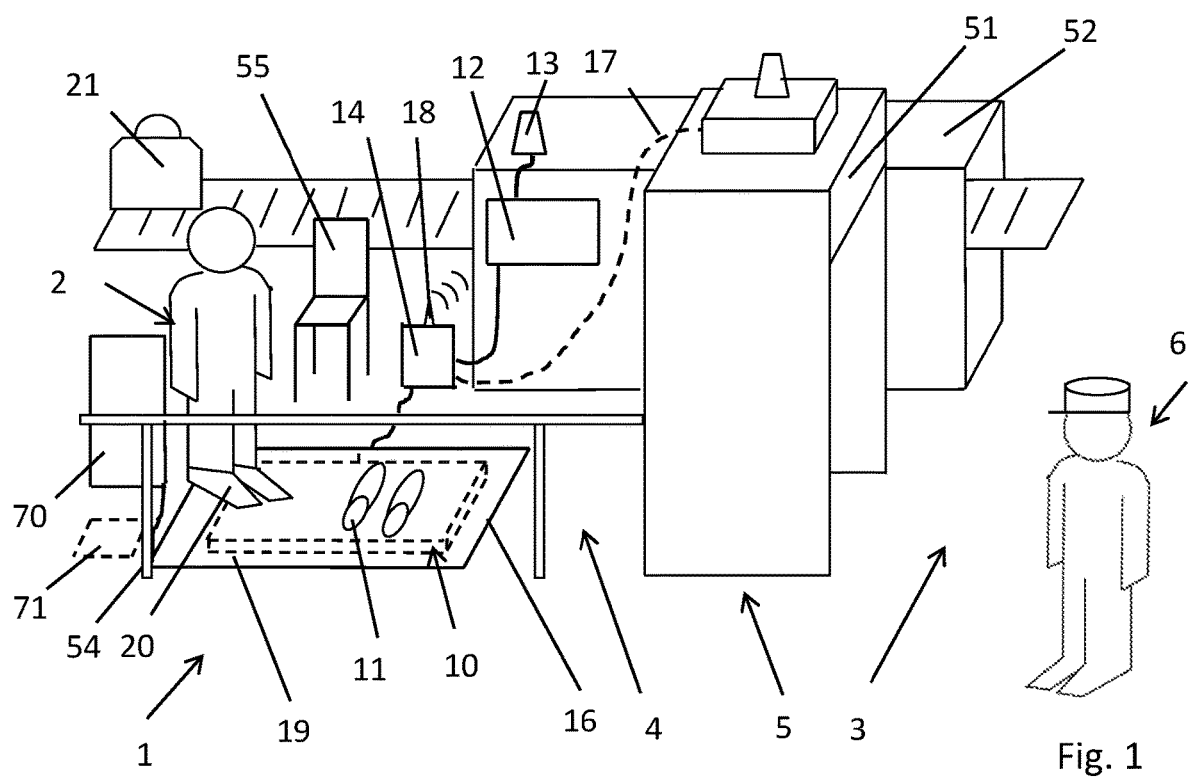
FIG. 1 shows a view of a person in the path to a security portal of a restricted area provided with a shoe and a waist detection system, according to the invention.

FIG. 1 shows an exemplary restricted access area 3 of a facility of transportation such as an airport.

The restricted access area is a predefined zone whose access is limited to a group of persons, e.g. passengers of the facility of transportation, who are subjected to a security check for detecting problematic objects. The restricted access areas are thus provided with one or more accessing points, each accessing point being equipped with one or more security portals 5 for detecting dangerous and illegal objects and substances worn or carried on the body of people wanting to access the restricted area.

The security portal 5 comprises machines 51, 52 for detecting metal and dangerous substances in clothes, in shoes or in/on the body of a person as well in objects carried by the person, e.g. baggage, suitcase, handbags, and laptops.

The security portal 5 comprises a body scanning system 51 destined to scan the entire body of a person by means of harmless technologies, and an object scanning system 52 destined to scan such as bags, jackets, electronic equipment, etc. The object scanning system 52 could also be based on harmful technologies providing more efficient detection than harmless technologies.

In the exemplary embodiment of the FIG. 1, the body scanning system 51 and the object scanning system 52 comprise fixed installations positioned on a path 4 towards the restricted area 3, e.g. a gate-shaped body scanner 51 and an X-ray baggage detector 52 having a conveyor belt. The security portal 5 can further comprise portable or transposable devices for detecting specific dangerous or illegal objects and substances.

The path 4 to the restricted area 3 can be physically delimited by barriers 54 and obstacles, e.g. the X-ray baggage detector 52 with its conveyor belt, so as to manage the flow of persons through the security portal 5.

Persons wanting to access the restricted access area 3 are thus prompted to put their belongings, such as baggage 21, suitcase, handbag, and laptops, on the conveyor belt of the object scanning device 52 for security scan.

Persons are also prompted to remove such clothes components and garnishes that are known to be made of, or to comprise, inert metallic parts for carrying on a shape and/or substance-based security scanning, notably via the object scanning device 52. Other clothes components and garnishes, such as belts and jackets, that the person can easily and comfortably takes off, are to be removed and placed on the conveyor belt for security scanning.

Shoes are processed in a different way, since:
shoes and footwear do not necessarily comprise metallic parts; and
the removal of worn shoes requires time, as well as dedicated places to sit in both the public area and in the restricted area for allowing the removal and the putting on of the shoes.

The systematic obligation to remove shoes and footwear before going through the security portal generates a systematic delay for passing the security check, as well as additional time for removing the shoes and generates a bottleneck and blockage at the seating place when a crowd or flux of persons simultaneously goes through the security portal, as in most airports.

Moreover, a systematic obligation is uncomfortable for many people, notably for person having physical handicaps or limited movement due to aging.

Figure 4:
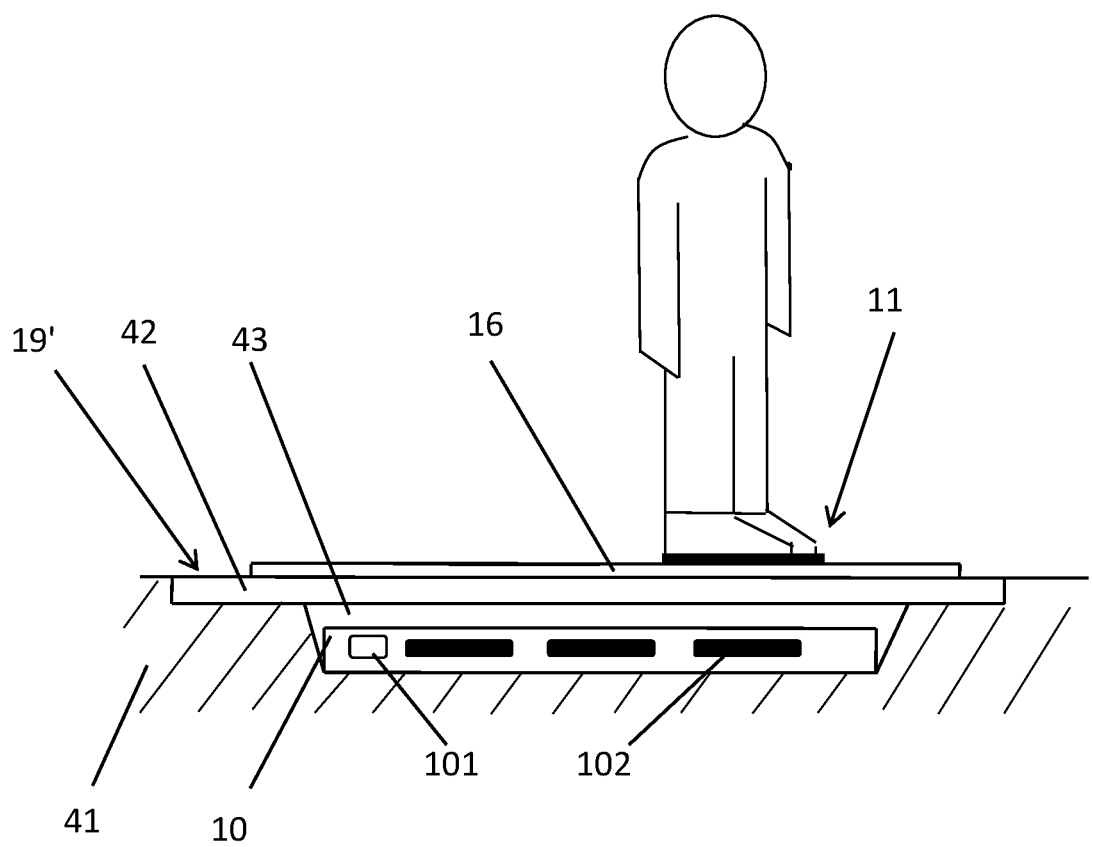
FIG. 4 illustrates an alternative embodiment of the system of FIG. 1, according to the invention.
Figure 5:
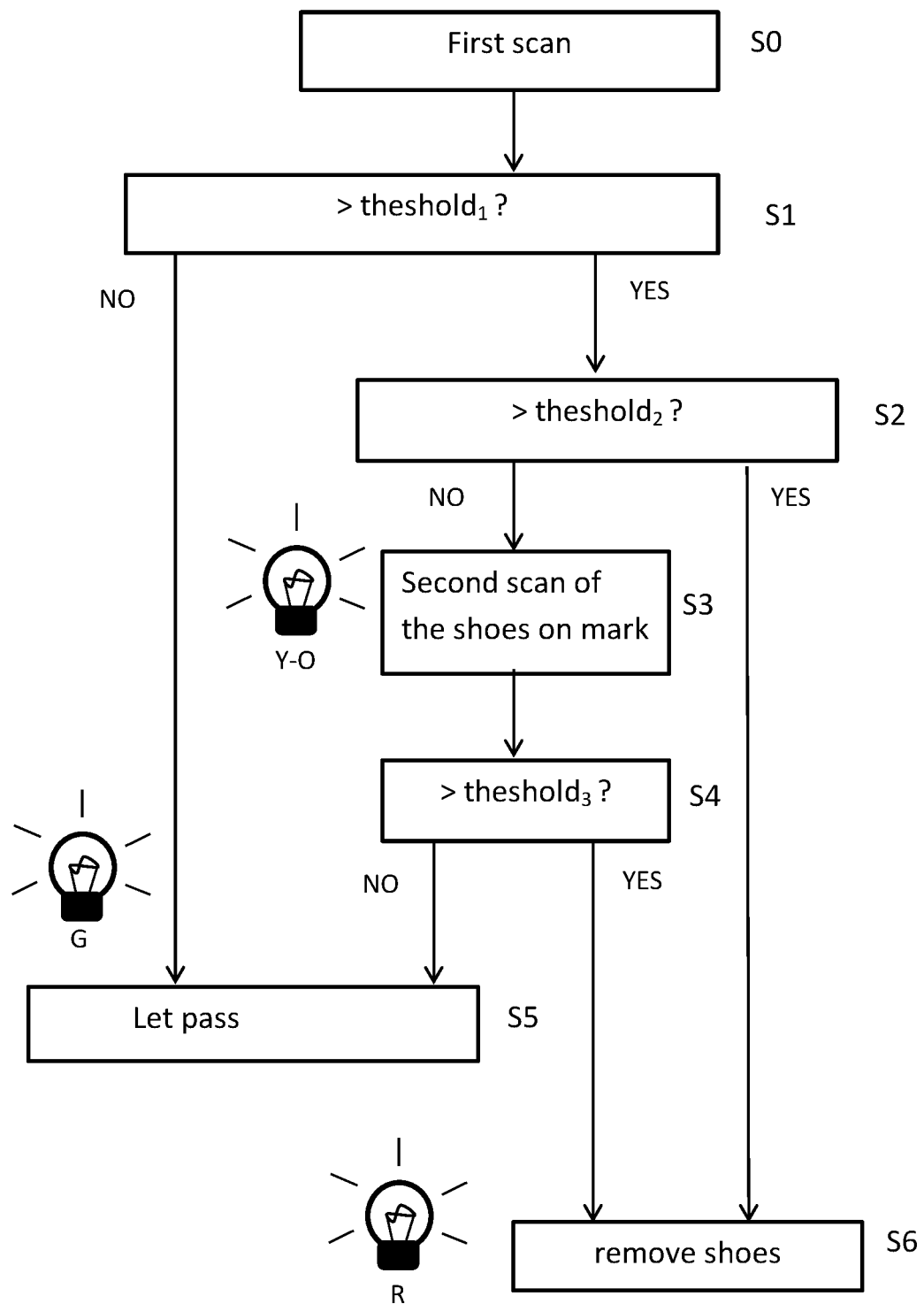
FIG. 5 illustrates a schematic representation of the sequences of the detection, according to the invention.

In order to limit such inconvenience, without reducing the security levels, the proposed method and system rely, as illustrated in FIGS. 1 and 4, on a pre-scanning of the shoes 20 worn by the person 2 on the path 4 to the security portal 5. This pre-scanning does not need to be reliable and a limited number of false negatives is acceptable, since reliable scanning will be performed anyway by the security portal 5. Its aim is to detect metallic objects (step S1) so as to prompt person wearing shoes considered to be likely to include metallic objects to remove them before passing through the security portal 5 (S6), thus reducing the number of people who need to pass twice through the portal. The pre-scanning thus does not require that the person places his feet at an accurate position, and only requires him to walk normally onto a detection surface on the floor, for example onto a carpet or surface covering the detector.

The scanning wearing shoes comprises a first scan (or pre-scanning) of the shoes worn by the person while walking on a path towards the security portal (S0). If metal is detected, they are requested to remove their shoes. In case of uncertainty, the user is requested to place his feet on or close to a position identified by marks in order to ensure the accurate (a more accurate) positioning of the shoe with respect to the same metal detector, and a second scan (or re-scanning) (S3) of the shoes is performed.

The early assessment of the potential presence of metallic objects within worn shoes of persons so as to prompt the person to remove his shoes before going through the security portal for the first time permits an efficient reduction of the number of persons who have to come back through the security portal. Each time a person has to come back this creates an interruption of the flow of persons through the security portal to allow the person to return to the public zone, to remove his shoes and to pass once more through the security portal. Each additional pass through the security portal causes a waste of time, not only for person wearing the shoes or footwear with unproblematic metallic components or garnishes, but also for persons waiting on the same path.

The two-stage scanning of the shoes worn by the person, i.e. the first (i.e. pre-scanning) and the second scan (i.e. rescanning) of the shoes at a predefined position, contributes to a rapid and comfortable passage of the flow of persons through the security portal. In fact, the first scan does not affect the transition of persons as executed while the person is walking or standing before the security portal without requiring specific actions or behavior from persons under scan. Only the persons wearing shoes considered problematic are subjected to the second scan that requires the user to position his shoes at the specific position.

The proposed method and system provide a reliable security scan of persons as they provide a hint of the problematic presence of metal objects within the shoes of a person wanting to access a restricted access area through the security portal. The detection of dangerous and illegal objects worn or carried by a user relies on the security portal scanner.

Moreover, the early-stage detection of potentially problematic shoes allows those shoes to be scanned separately through the security portal, in particular by means of scanning system 52 designed to scan objects. This permits, on the one hand to carry out the scan of the barefoot person and the scan of his shoes at the same time, and on the other hand, to take advantage of the most efficient detections of illegal and dangerous objects and substances provided by up-to-date object scanning systems, e.g. x-ray detector.

Furthermore, the proposed method and system are intrinsically compatible with most existing accessing paths and security portals of facilities and buildings, without requiring complex and bulky installations.

FIG. 1 shows an exemplary embodiment of the security portal 5 equipped with a system 1 configured to scan the person 2 before access to the restricted access area 3 through the security portal 5, according to the invention.

The system 1 comprises a surface 19,19' onto which a person can walk, a metal detector 10 configured to detect a metal object in the shoes 20 worn by the person when the person walks on said surface 19,19', an indication unit 12, 13 for providing instructions to the person 2, directly or through an assistant 6 operating at the security portal 5, and a processing unit 14 controlling the metal detector and the indication unit.

Advantageously, the surface 19,19' onto which the person can walk while being scanned by the metal detector is located in the path 4 towards the security portal 5 so that the persons would instinctively walk and stand on the surface 19 where the first scan (i.e. pre-scan) is operated on the shoes. Preferably, the surface 19,19' is located in front of the conveyor belt of the baggage detector 52 so as to cause the person to walk and to stand on the surface when preparing and placing his baggage on the conveyor belt for control.

Advantageously, the barriers 54 and obstacles physically delimiting the path 4 could be arranged to direct the user inside the operational range of the metal detector.

The surface can be an upper surface 19 of the metal detector, e.g. a surface of a cover 15, a lid or a top portion of the casing of the metal detector.

Alternatively, as shown in FIG. 4, the surface can be an upper surface 19' provided by an element that is not part of the metal detector, such as a plate 42, a portion of a floor or supporting structure located above or on the metal detector. In fact, the metal detector 10 could be located in a recess 43 of a floor 41 on the way to the security portal and covered by a floor plate 42. The floor plate 42 would thus provide the surface 19' onto which a person can walk during the first and second scan.

Figure 3A:
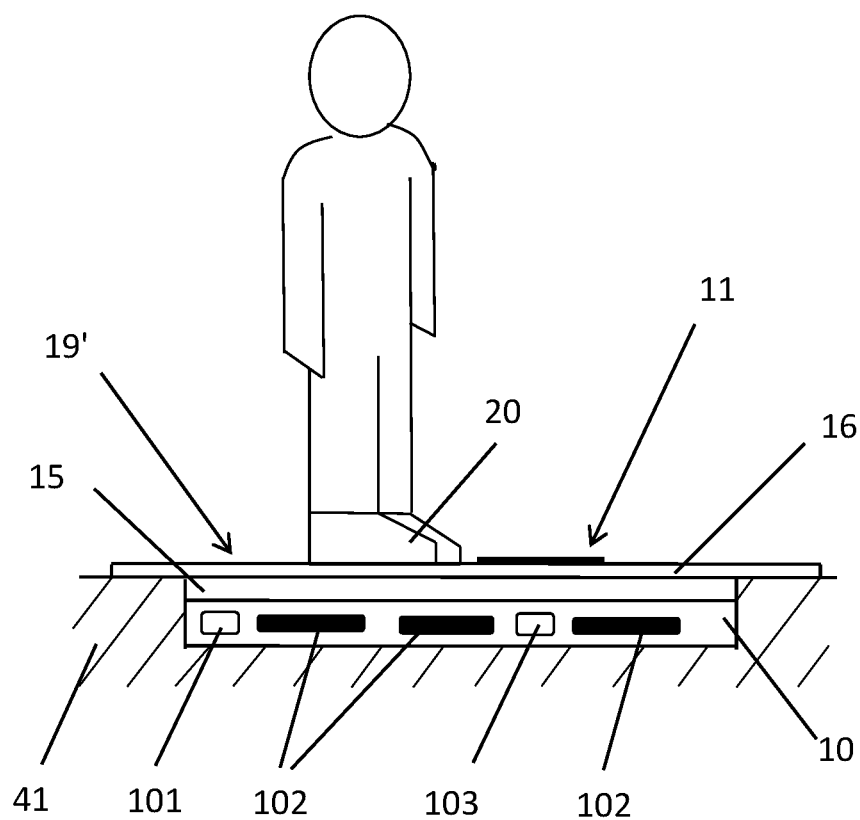
FIG. 3a shows an exemplary situation of a first scan (or pre-scan) of the shoes worn by a person by means of the detection system of FIG. 1.

The metal detector 10 comprises a plurality of coils 102 parallel to said upper surface 15, and a circuit 101 for detecting a variation of self-inductance of each coil and/or a variation of the coupling between coils among the plurality of coils 102 when a metallic part is moved in the vicinity of said coil, as illustrated by FIGS. 3a,b. Advantageously, the circuit 101 can further be configured to detect a variation of the coupling between coils and solid-state magnetic sensors located within the metal detector.

The excitation signal fed to the coil to perform the above-mentioned measurements is typically periodic, and may contain several frequencies. The raw output of the metal detector is a multi-dimensional signal, with typically in-phase and out-of-phase components for each measurement frequency.

As the system has to provide a hint of a potential presence of a metallic object, the metal detector does not necessarily have to implement complex detection principles, such as nuclear magnetic resonance or millimeter wavelength technologies. The coils could thus be excited by frequencies that are lower than those required by such mentioned technologies, e.g. by a frequency within a range of 1-100 KHz, e.g. 10 kHz.

In the exemplary embodiment of the FIGS. 3a,b, the metal detector is a flat metal detector of 60 cm×90 cm×10 mm. The metal detector comprises a protective cover 15 made of plastic.

The system further comprises a mark element 11 spatially cooperating with the metal detector so as to provide an indication of a specific position on the surface 19, 19', so as to define a specific position of the shoes with respect to the metal detector. Advantageously, the mark can have the form of a footprint 11 or a pictogram indicating the soles of a pair of shoes.

The mark provides an indication for the positioning of the shoes within a space wherein the metal detector is configured to be (more) efficient in detecting a presence of a metal object.

The mark 11 can be located directly on a portion of the surface 19,19'. Alternatively, the mark 11 can be placed, located or painted on a distinct element positioned above the surface 19,19', advantageously on a removable flat element such as a rug or a carpet 16.

In the illustrated exemplary embodiment, the mark 11 is in the form of a footprint indicating a specific position on a non-slip carpet 20. The use of such a mobile element facilitates the installation, the calibration and the tuning-of the system 1. Moreover, the carpet 20, notably in the form of a textile carpet, permits the metal detector to be hidden with an informal and familiar component so as to avoid hesitations, doubts and distractions of persons walking or standing over it.

The system further comprises one or more proximity detectors 103. The proximity detector measures the position of a body part relative to the metal detector, even in the absence of metal in said body part. In the case of detection of metal in shoes, two such detectors can be used to ensure the two feet of the passenger are correctly placed on the specific position 19. Said proximity detector can be optical and/or electromagnetic proximity detectors. An electromagnetic proximity sensor typically detects a variation in the capacitance or capacitive coupling between electrodes embedded within the metal detector. Optical proximity detectors can for example be realized by processing images from a video camera or other methods known in the field such as beam interruption, triangulation or LIDAR.

The system is configured to assess a probability of a presence of metal based on signals from the metal detector (i.e. from the circuit 101) and, advantageously, from the proximity detector 103.

Figure 3B:
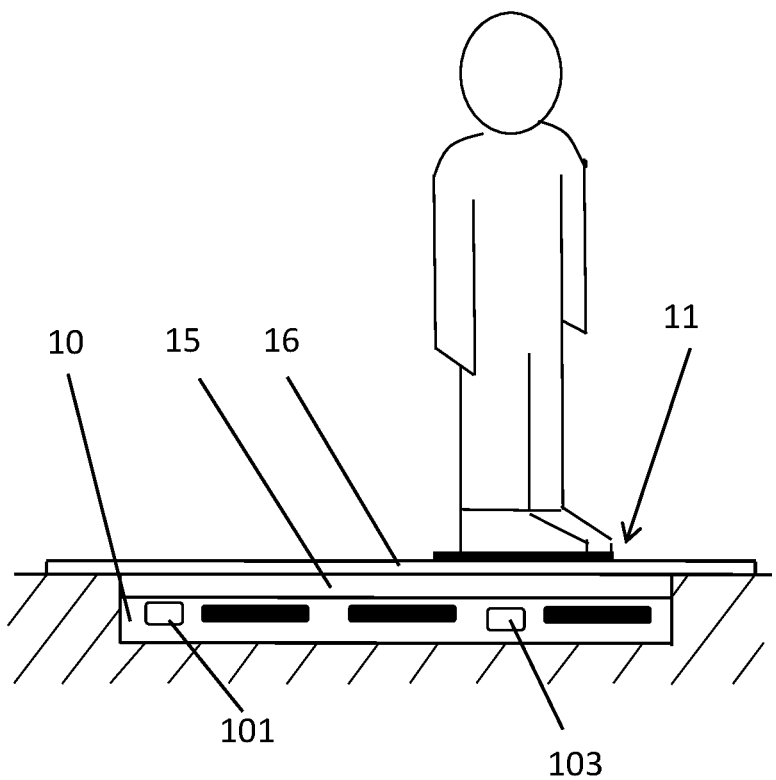
FIGS. 3b shows an exemplary situation of a second scan (or rescan) of the person's shoes by means of the detection system of FIG. 1.

The processing unit 14 of the system 1 is configured to control the metal detector 10 and the indication unit 12, 13 for:
 a) letting the person walk towards the restricted area if a first scan of the person's shoes indicates a probability of a presence of metal lower than a first threshold;
 b) prompting the person to position his feet close to the mark 11 if the first scan of a person's shoes (FIG. 3a)

indicates a probability of a presence of metal higher than the first threshold, in order to carry out a second scan of said shoes close to said mark (FIG. 3b),
 c) prompting the person to remove his shoes if the first scan indicates a probability of a presence of metal higher than a second threshold, or if the second scan indicates a probability of a presence of metal in the shoes higher than a third threshold.

A probability of a presence of metal (e.g. metal object) lower, respectively higher, than a threshold can be determined by comparing a detection result provided by the metal detector or computed by the processing unit with an explicitly defined threshold, e.g. a detection threshold.

Alternatively or complementarily, a probability of a presence of metal lower, respectively higher, than a threshold can also be determined by an implicitly defined threshold. A probability of a presence of metal lower, respectively higher, than a threshold can thus be based on thresholding, weighting or classifying a plurality of sensed values provided by the metal detector, e.g. multi-dimensional measures and/or multi-spatial measures provided by detections coils 102 of the metal detector, in particular along or with respect to the surface 19, 19' onto which the person walk. A probability of a presence of metal lower, respectively higher, than a threshold can thus be determined by means of a multidimensional boundary or classifier. A probability of a presence of metal lower, respectively higher, than a threshold can thus be determined by means of a machine learning system, e.g. a clustering or multi-output artificial neuronal network.

Advantageously, a probability of a presence of metal lower, respectively higher, than a threshold can be determined by a classifier using signals from the metal detector (i.e. metal detecting circuit 101) and from the proximity detector 103. Advantageously, the classifier is configured to classify a probability of a presence of metal in several classes, notably:
 i) a probability of a presence of metal that is below a first threshold, preferably the threshold being lower than the threshold used by the metal detector of the security portal (e.g. the walk-through gate);
 ii) a probability of a presence of metal that is higher than a second threshold, the second threshold being higher the threshold used by the metal detector of the security portal;
 iii) a probability of a presence of metal in between the first and the second threshold.

Advantageously, the classifier operates not only on currently fed signal but also on previously generated signals, preferably within a sliding time period, for determining a probability of a presence of metal. Optionally, the signals fed to the classifier are previously filtered, e.g. for removing artifacts and outliners. Transitions between classes may be accompanied by visual, tactile or audible alarms, notably trough the indication unit 12, 13.

A seating area, e.g. with one or more chairs 55, could be positioned near, advantageously in front of the mark 11, so as to permit the prompted persons to remove their shoes. As a minority of the pre-scanned persons are subjected to the second scan, the number of sitting places could be limited to a few units without causing a bottleneck or blockage of the flow of persons on the way to the security portal.

The indication unit of the system can comprise a display unit, preferably a color display 12, so that the processing unit could prompt the person by displaying alphanumerical texts, preferably combined with colored backgrounds, icons and/ or animations illustrating the prompted actions. Advantageously, the display unit can be a touchscreen further providing an input user interface to the system 1, in particular through the processing unit 14. The display unit can be, or comprise, an e-ink screen.

Figure 2A:
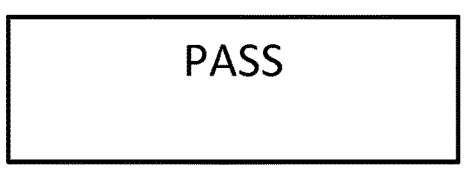
FIGS. 2 a-c illustrate exemplary instructions provided by the shoe detection system, according to the invention.
Figure 2A:
Figure 2B:
Figure 2B:
Figure 2C:
Figure 2C:

The person walking or standing on the surface 19, 19' could thus be prompt by:
- a pass message (e.g. FIG. 2a) allowing the person to walk towards the restricted area;
- a warning message (e.g. FIG. 2b) to prompt the user to position his shoes on the mark for carrying out the second scan (i.e. re-scan);
- a remove message (e.g. FIG. 2c) to prompt the user to remove his shoes before continuing towards the restricted area.

Advantageously, the indication unit can comprise a luminous element, such as a lighting element 13, for providing information to the assistant 6 surveying the operations at the security portal. The processing unit could thus inform the assistant 6, for example by irradiating:
- a green light simultaneously to the pass message;
- a yellow/orange light simultaneously to the warning message;
- a red light simultaneously to the remove message.

The method and the system can envisage to modify the detection sensitivities of the metal detector during the first and/or the second scan.

The sensitivities can be modified, for example by modifying one or more parameters related to the electromagnetic excitation and/or reception of one or more coils of the metal detector. Typical parameters are frequencies and amplitudes of excitation signals and amplification gain or filtering attenuation of sensed signals.

Alternatively or complementarily, the method and the system can envisage modifying the first, second and/or third thresholds related to a probability of a presence of a metal, e.g. metal object.

A modification of the first, second and/or third thresholds can be realized, e.g. by modifying detection thresholds, boundaries, and/or weighting and classification parameters.

In case of machine learning, a modification of the first, second and/or third thresholds can occur by implementing a pre-defined set of parameters or by updating the machine learning by a new set of training data, e.g. based on detection events occurred at the system and/or at the security portal.

In the case of the described classifier, a modification of the first and/or second threshold can occur by modifying the decision boundaries of the classifier.

Advantageously, the modifications are function of events occurred at the security portal, notably correlated with passages of persons not prompted to remove his shoes before to pass through the security portal. In particular, the modifications are functions of a presence of an alarm associated with a passage of these persons, advantageously including alarm level and position of the detected metal (height and left/right position). These events can have form of event numbers and rates, e.g. communicated directly, through a remote server or manually by an operator. Alternatively or complementarily, the events can have form of (raw) metal detection signals provided by the security portal, e.g. through a connection 17 connecting the security portal and the system 1.

The modifications can be, alternatively or complementarily, function of events correlated with scanning of persons executed by the system 1, e.g. rates or numbers of supposed presence of metal objects within worn shoes. The modifications can thus be function of:
- number of second scan (re-scan) with respect to the number of first scan (pre-scan), e.g. in a predefined period; and/or
- rates or numbers of persons being prompted to remove his shoes with respect to the number persons being scanned by the system, e.g. in a predefined period.

The modifications can be further function of statistical detection rates provided by a remote server. These rates could take into account the initial and/or final destinations of persons in case of transportations, e.g. mountain or seaside resorts. Alternatively or complementarily, these rates could take into account current season, e.g. winter or summer season, or local event, e.g. sport or professional meeting, that could condition the worn shoes or footwear of persons attending the security portal.

The system 1 can thus comprise an interface for adapting at least one of said thresholds or detection sensitivities by manually entering new values.

Advantageously, the system can comprise a communication module 17 for connecting the system to the security portal in order to adapt one or more of these thresholds or sensibilities, automatically and/or on request.

The communication module 17 can be configured to connect the detection systems of the security portal destined to scan the body of the persons for detecting metals, so as to receive detection rates related to the shoes/footwear worn and/or the lower body are of the shoe wearers passing through said security gate.

Advantageously, the systems could be configured to processing received rates in order to extract or estimate detection rates that are related to the shoes and footwear worn.

The system can comprise a wired or wireless communication module 18 for communication to a remote server for receiving and/or sending information related to shoe detection operations.

According to another aspect of the invention, the restricted access area 3 of the facility of transportation of FIG. 1 can, alternatively or complementarily to the shoes detector, comprise a waist detector 70 for scanning a waist portion of a person before access to the restricted access area.

The proposed system is arranged to provide an early assessment of the potential presence of metallic objects within other clothes components and garnishes, such as belts and watches, worn by persons so as to prompt the person to remove such objects before going through the security portal for the first time. As the case of the shoes detection, the reliability of the detection is ensured by the security portal which is used in any case for accessing the restricted area.

An early assessment permit to prompt the user to remove such potential problematic objects, permit a more rapid the flow of persons the security portal of a restricted access area. In fact, it reduces the number of persons who stop the flow of persons due to having to come back through the security portal as having forgotten to remove a belt with metallic parts, a watch, a key holder or a phone from a pocket.

Moreover, the system can provide thus a more rapid flow of persons through the security portal of a restricted access area by asking person to remove such object uniquely if such objects are early assessed as potential problematic by the system. Person would thus not lose time for removing inert objects while being in the path to the security portal.

The early detection of the waist portion of persons is also based on a two-stage scanning, i.e. a first (or pre-scanning) of a waist portion of the user walking on a path to the security portal followed, in case of inconclusive results, by a second scan (or rescanning) of the waist portion at a predefined position. The 2-step detection approach contributes to a rapid and comfortable passage of the flow of persons through the security portal. In fact, only the persons wearing or carrying objects considered problematic are affected by the second scan that requires a predefined positioning of the person with respect to the waist detector 70.

The exemplary embodiment of FIG. 1 illustrates a metal detector 70 configured to detect a metal object worn or carried by the person in his waist region when the person walks on the way 4.

The waist detector is positioned along the way 4 so as to scan the waist region of person that is waiting or preparing itself for passing the security portal. Advantageously, the waist detector is operatively located near the object scanning detector 52 for avoiding the person to come back for placing detected potential problematic objects on the convoy belt for scanning.

In the exemplary embodiment of FIG. 1, the waist detector is located near the convoy belt of the object detector 52 and vertically mounted, e.g., on the barrier 54 limiting the way to the security portal 5.

The system further comprises a mark 71 for indicating a specific positioning for the person for carrying on the second scan. The mark 71 can be located (or paint) on a surface of the way to the security portal on which the person can walk and stand.

Figure 6:
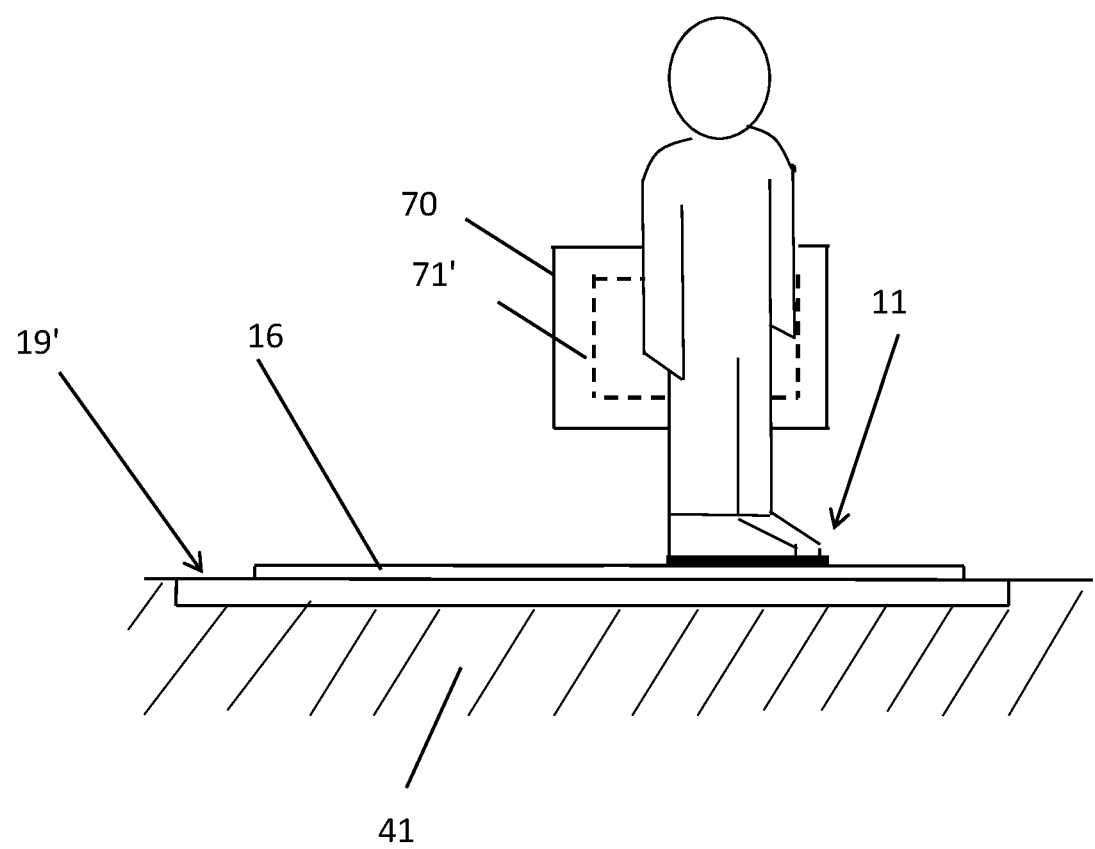
FIG. 6 shows a variant of the waist detector of FIG. 1.

In the embodiment of FIG. 6, the mark 71' is located on a surface along the way 4, in particular on a vertical surface, so as to indicate the specific positioning with respect to the detector 70. The vertical surface can be a dedicated vertical surface or a surface of the waist detector itself.

Eventually, a single or combined mark can be used for indicating a specific positioning for both rescan of shoes and waist of the person.

A single proximity sensor can be used to ensure the waist portion of the passenger is correctly placed on the specific position, eventually located in the casing of the metal detector 70.

The processing unit 14 is thus configured to further control the waist detector 70 and the indication unit 12, 13 for:
  a) allowing the person to walk towards the restricted area if a first scan of a waist portion of person indicates a probability of a presence of metal lower than a first threshold;
  b) prompting the person to place itself close to the position indicated by the mark 71 if the first scan of the waist of the person indicates a probability of a presence of metal higher than the first threshold, in order to carry out a second scan of his waist portion close to said mark,
  c) prompting the user to remove objects from his waistline if the first scan indicates a probability of a presence of metal higher than a second threshold, or if the second scan indicates a probability of a presence of metal in the waist portion of the person higher than a third threshold.

As for the shoes metal detector, the detection sensitivities of the waist metal detector 70 during the first and/or the second scan as well as the first, second and/or third thresholds related to a probability of a presence of a metal can be modified.

Advantageously, the modifications are function of events occurred at the security portal, notably detection alarms correlated with metallic objects located at the waist level, such as watches, belt, phones and key holder.

According to an independent aspect of the invention, the invention concern a self-learning metal detection for method and a system providing an early assessment of the potential presence of metallic objects within shoes and/or other clothes components and garnishes worn or carried by persons. Person wearing problematic shoes and/or carrying problematic objet are thus prompted to remove such shoes and/or objects before going through the security portal for the first time.

The self-learning metal detection is configured to adapt and/or modify detection sensitivities and/or assessment according to a feedback provided by the security portal.

The system is arranged for scanning a person before access to a restricted access area through a security portal and comprises:
  a metal detector configured to detect a metal object in the shoes worn by the person and/or a metal object located in a waist portion of the person when the person walks on said surface;
  an indication unit for providing instructions to the person, directly or through an assistant; and
  a processing unit controlling the indication unit for prompting the user to remove his shoes and/or objects from his waist region if a scan of the person's shoes and/or of a waist portion of the user indicates a probability of a presence of metal higher than a threshold,
  wherein the system is further configured to receive data from the security portal, the data being related to detection of metal worn or carried by persons at the security portal;
  and wherein the system is configured to modify detection sensitivities of the metal detector and/or the threshold in function of received data.

The method concerns a scanning a person for accessing a restricted access area through the security portal, and comprises steps of:
  by means of a metal detector, scanning shoes worn by a person and/or a waist portion of the person on a path to a security portal; and
  in response of a detection supposing a presence of a metal object in the shoes and/or in said waist region, prompting the person to remove his shoes and/or object before to pass through the security portal;
  wherein
  said step of scanning the shoes comprises steps of:
  modifying detection parameters in function of detection data provided from the security portal.

Advantageously, the provided data comprises occurrences and/or rates of alarms associated with a passage of person through the security portal, advantageously including alarm level and position of the detected metal (up/mid/lower level and left/right position). These events can have form of event numbers and rates, e.g. communicated directly, through a remote server or manually by an operator. Alternatively or complementarily, the events can have form of (raw) metal detection signals provided by the security portal, e.g. through a connection connecting the security portal and the system.

The detection of shoes and/or waist can be based on a single step or 2-step detection approach.

Advantageously, the system further comprises one or more proximity detectors. The proximity detector measures the position of a body part of the person relative to the metal detector, even in the absence of metal in said body part, in particular a positioning of the shoes and/or of the waist portion of the person on the way to the security portal.

Said proximity detector can be optical and/or electromagnetic proximity detectors. An electromagnetic proximity sensor typically detects a variation in the capacitance or capacitive coupling between electrodes embedded within the metal detector. Optical proximity detectors can for example be realized by processing images from a video camera or other methods known in the field such as beam interruption, triangulation or LIDAR.

The probability of a presence of metal lower, respectively higher, than a threshold can also be determined by a classifier that operate on signals from the metal detector and from the proximity detector(s). In case of a single step detection approach, the classifier is configured to classify a probability of a presence of metal in, preferably, 2 classes, wherein the first class comprises probabilities of a presence of metal that are below a first threshold, preferably the threshold being lower than the threshold used by the metal detector of the security portal (e.g. the walk-through gate);
and wherein the second class comprises the others probabilities.

In case of a 2-step detection approach, the classifier is configured to classify a probability of a presence of metal in, at least, 3 classes:
i) a first class representing a probability of a presence of metal that are below a first threshold, preferably the threshold being lower than the threshold used by the metal detector of the security portal (e.g. the walk-through gate);
ii) a second class representing a probability of a presence of metal that is higher than a second threshold, the second threshold being higher the threshold used by the metal detector of the security portal;
iii) a third class representing a probability of a presence of metal in between the first and the second threshold.

The classifier is a self-learning classifier that uses the provided data from the security portal, in particular in form of labeled data, for adapting his classification boundaries and weighting.

In particular in the case of a 1-step approach, the self-learning classifier is configured to modify the weighting of the signals provided by the proximity sensor(s) so as to permit a detection of person walking or standing on the way to security portal without imposing him a predefined (and temporarily immobile) position for scanning his shoes and/or waist portion. A plurality of proximity sensors located on the way to the security portal permits to compensate the position incertitude about the shoes and/or the waist portion of the person on the way to the security portal.

LIST OF REFERENCE NUMERALS

1 Shoe scanning system
10 Metal detector
101 Detecting circuit
102 Coil
103 Proximity sensor
11 Footprint
12 Display
13 Lamp
14 Processing unit
15 Cover of the metal detector
16 Carpet
17 Communication link
18 Wireless communication module
19,19' Walking and standing surface
2 Passenger
20 Shoes or Footwear
21 Suitcase
3 Restricted area
4 Access Path to the security portal
41 Floor
42 Floor plate
43 Recess
5 Security portal
51 Body scanner
52 X-Ray baggage scanner
54 Barrier
55 Chair
6 Assistant
70 Waist detector
71, 71' Positioning mark
G, Y-O, R Green, Yellow/Orange, and Red light
S0 Step of scanning the shoes worn by a person walking on a path to a security portal
S1 Assess the probability of the presence of a metal object and compare it with a first threshold
S2 Compare the probability of the presence of a metal object with a second threshold higher than the first threshold
S3 In the case of the probability of the presence of a metal object between the first and the second threshold, prompting the person to place his shoes on the mark and rescan the shoes on the mark
S4 Assess the probability of the presence of a metal object and compare it with a third threshold
S5 Prompting the person to continue to the security portal
S6 Prompting the person to remove his shoes before continuing to the security portal

The invention claimed is:
1. A system for scanning a person before access to a restricted access area, the system comprising:
a surface onto which a person can walk;
a metal detector configured to detect a metal object in the shoes worn by the person and/or a metal object located in a waist portion of the person;
a position identifying mark indicating a specific position of said surface with respect to the metal detector;
an indication device for providing instructions to the person, directly or through an assistant; and
a processing device for controlling the indication device:
wherein the metal detector is configured to perform a first scan on-the-fly when the person is walking on said surface and a second scan when the person stands at said position identifying mark, and wherein the processing device is configured for:
a) prompting or allowing the person to walk towards the restricted area if the first scan of the person's shoes and/or of the waist portion of the person performed by the metal detector indicates a probability of a presence of metal lower than a first threshold;
b) prompting the person to place his feet and/or himself at said position identifying mark if the first scan of the person's shoes indicates a probability of a presence of metal higher than the first threshold, in order to carry out, by means of the same metal detector, the second scan of said shoes and/or of said waist portion, or
c) prompting or allowing the person to remove his shoes and/or remove objects from his waist portion if the first scan indicates a probability of a presence of metal higher than a second threshold, or if the second scan indicates a probability of a presence of metal in the shoes and/or in said waist region higher than a third threshold.

2. The system of claim 1, further comprising at least a proximity detector for detecting a positioning of the shoes and/or the waist portion of the person at the specific position.

3. The system of claim 1, wherein the metal detector comprises a plurality of coils parallel to said surface, and a circuit for detecting a variation of self-inductance of each when a metallic part is moved in the vicinity of said coil.

4. The system of claim 1, wherein said surface is an upper surface of the metal detector.

5. The system of claim 1, wherein the mark displays a picture of footprint, preferably the mark indicating a specific position on a carpet located on at least a portion of said surface.

6. The system of the claim 1, comprising an interface for adapting at least one of said thresholds by manually entering new values.

7. The system of the claim 1, comprising a communication module for connecting it to a metal detection portal in order to adapt at least one said thresholds automatically.

8. The system of claim 7, said communication module being arranged for receiving a detection rate from the security portal, said detection rates being related to worn shoes, footwear and/or lower body region of shoe-wearing users passing through said security gate.

9. The system of claim 1, the processing device being arranged to modify:
   a detection sensitivity of the metal detector during the first and/or second scan, and/or
   a first and/or second and/or third threshold;
the modification being a function of computed rates of supposed presence of metal objects and/or the received detection rate from the security portal.

10. A method for scanning a person before accessing a restricted access area through a security portal, the method comprising steps of:
   by means of a metal detector, scanning shoes worn by a person and/or scanning a waist portion of the person when said person is walking on a path to a security portal; and
   in response of a detection of likely presence of a metal object in the shoes and/or in said waist portion, prompting the person to remove his shoes and/or to remove objects from his waist, in order to scan the person separately from his shoes and/or said objects through the security portal;
   wherein said step of scanning the shoes and/or said waist portion comprises steps of:
   performing a first scan on-the-fly of the shoes worn by the person and/or waist portion of the person walking on said path to the security portal by means of the metal detector so as to provide a detection result; and
   in response of a detection result indicating a likely presence of a metal object:
   prompting the person to stand so as to place his shoes and/or itself and/or his waist at a specific position with respect to the metal detector, said specific position being indicated by a position identifying mark; and
   performing a second scan of the shoes by means of the same metal detector for detecting a presence of a metal object within the worn shoes and/or within the waist portion of the person standing at said specific position.

11. The method of claim 10, further comprising a step of modifying:
   a detection sensitivities of the metal detector during the pre-scan and/or the rescan, and/or
   thresholds of detection results for supposing a presence of metal objects.

12. The method of claim 11, the modification being a function of computed rates of supposed presence of metal objects in a predefined period, a detection rate provided from the security portal and/or statistical detection rates provided by a remote server.

13. The method of claim 10, further comprising physically delimiting the path to the security portal so as to conduct the person inside an operational range of the metal detector.

14. The method of claim 10, further comprising a step of:
   in response of a detection result of the rescan supposing a presence of a metal object within the shoes, separately scanning said shoes and/or objects through the security portal.

15. The method of claim 10, wherein said step of rescanning comprises a step of detecting a positioning of the shoes and/or the waist portion of the person at the predefined position, preferably by means of at least a proximity detector.

\* \* \* \* \*